United States Patent [19]
Mane et al.

[11] Patent Number: 5,712,132
[45] Date of Patent: Jan. 27, 1998

[54] METHOD FOR THE ENZYMATIC PREPARATION OF AROMATIC SUBSTANCES

[75] Inventors: Jean Mane, Grasse; Joseph Zucca, Antibes, both of France

[73] Assignee: V. Mane Fils S.A., Bar-Sur-Loup, France

[21] Appl. No.: 574,786

[22] Filed: Dec. 19, 1995

Related U.S. Application Data

[63] Continuation of Ser. No. 211,036, filed as PCT/FR93/00745 Jul. 21, 1993, abandoned.

[30] Foreign Application Priority Data

Jul. 24, 1992 [FR] France .................. 92 09174

[51] Int. Cl.$^6$ .................. C12P 7/42; C12N 9/02
[52] U.S. Cl. .................. 435/147; 435/189
[58] Field of Search .................. 435/147, 189; 568/442, 425; 549/436

[56] References Cited

U.S. PATENT DOCUMENTS

| | | | |
|---|---|---|---|
| 3,635,828 | 1/1972 | Benjamin et al. | 252/99 |
| 4,708,964 | 11/1987 | Allen | 514/533 |
| 4,733,002 | 3/1988 | Yokoyama et al. | 560/55 |
| 4,874,701 | 10/1989 | Cooper | 435/147 |
| 5,087,417 | 2/1992 | Dumbroff et al. | 422/1 |
| 5,128,253 | 7/1992 | Labuda et al. | 435/147 |
| 5,262,315 | 11/1993 | Gross et al. | 435/147 |
| 5,279,950 | 1/1994 | Labuda et al. | 435/147 |

FOREIGN PATENT DOCUMENTS

| | | |
|---|---|---|
| 0233570 | 2/1987 | European Pat. Off. . |
| 0453368 | 4/1991 | European Pat. Off. . |

OTHER PUBLICATIONS

Josephson et al. (1985) *J. Food Sci.*, 50, 5–9.
Mtebe et al. (1987) *Food Chem.*, 23(3), 175–82, in *Chem Abst.*, 106, 547, Abst #212647.
Yoshimoto et al., JP 02,200,192, 8 Aug. 1990, in *Chem. Abst.* 114, 575, Abst #22487.
Koshihara et al. (1984) *Biochem. Biophys. Acta*, 792, 92–97.

*Primary Examiner*—Michael G. Witshyn
*Assistant Examiner*—Jon P. Weber
*Attorney, Agent, or Firm*—Larson & Taylor

[57] ABSTRACT

A method for preparing aromatic substances having formula (I), wherein a substrate of formula (II) or an isomer of these precursors, also termed a substrate, in particular selected from those of formula (III), in which formulae $R_1$ may be a $-CH_3$, $-CH_2OH$, $-CHO$, $-COOH$, or (a) radical, $R_2$ may be a $-H$, $-OH$ or $-O-CH_3$ radical $R_3$ may be a $-H$, $-OH$ or $-O-CH_3$ radical, and $R_2$ and $R_3$ may form a methylenedioxy bridge (b), is exposed to the activity of a lipoxygenase.

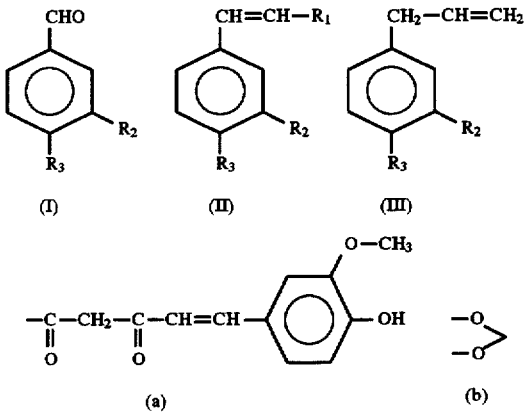

20 Claims, 3 Drawing Sheets

METHOD FOR THE ENZYMATIC PREPARATION OF AROMATIC SUBSTANCES

This application is a continuation of application Ser. No. 08/211,036 filed as PCT/FR93/00745 Jul. 21, 1993, now abandoned.

The subject of the invention is a method for the enzymatic preparation of some aromatic substances.

Aromatic substances is understood to refer to all substances used for the perfume which they release and/or the taste which they provide in the food, pharmaceutical or perfume industry.

The method in accordance with the invention makes it possible to prepare aromatic substances of formula:

in which
$R_2$ may be a radical —H, —OH, —O—$CH_3$,
$R_3$ may be a radical —H, —OH, —O—$CH_3$,
$R_2$ and $R_3$ may form a methylenedioxy bridge These aromatic substances advantageously belong to the group comprising: vanillin, benzaldehyde, anisaldehyde, para-hydroxybenzaldehyde, heliotropin and protocatechnic aldehyde.

BACKGROUND OF THE INVENTION

It was hitherto known to prepare vanillin according to various processes:
- chemically from guaiacol, but the vanillin is obtained in a mixture containing numerous impurities, because of which the yields are average;
- from the degradation of lignin, but obtaining vanillin in the pure state requires large consumption of chemical products and energy, and results in numerous ecologically toxic waste products;
- from safrole, a compound present in essence of sassafras, thus making it possible to obtain an isovanillin/vanillin mixture, two isomers which are difficult to separate;
- from eugenol, a compound present in oil of cloves, this compound being subjected to a first step of isomerization to isoeugenol (cis and trans in variable proportions) and then a second step of oxidation to give vanillin; however, this chemical process gives very average yields.

In addition, for all the processes of the prior art resorting to at least one chemical manipulation, the product obtained can only be called "synthetic or semisynthetic vanillin" and can in no way be called "vanillin of natural origin", even if the starting substrate is natural (the case of eugenol or safrole).

Regarding benzaldehyde, it is produced, for example, from cinnamaldehyde treated in alkaline medium under pressure and at high temperature (U.S. Pat. No. 4,617,419).

As regards anisaldehyde, it is conventionally produced by chemical oxidation of anethole, which is found in large quantities in essence of star anise.

However, just as for vanillin and for the same reasons, these two compounds cannot be qualified as "natural".

SUMMARY OF THE INVENTION

The aim of the invention is to overcome the disadvantages of the prior art and it proposes a biotechnological method which makes possible the preparation of some aromatic substances of good purity and with high yields.

Thus, the Applicant has had the merit of establishing that it was possible to prepare aromatic substances of formula:

by subjecting one of their precursors, called the substrate, corresponding to the formula:

or one of the isomers of these precursors, also called substrate, chosen especially from those corresponding to the formula:

in which
$R_1$ may be a radical —$CH_3$, —$CH_2OH$, —CHO, —COOH, $R_2$ may be a radical —H, —OH, —O—$CH_3$,
$R_3$ may be a radical —H, —OH, —O—$CH_3$,
$R_2$ and $R_3$ may form a methylenedioxy bridge to the action of an enzyme: lipoxygenase or lipoxidase.

This enzyme is itemized under the reference EC 1.13.11.12 in the work "Enzyme Nomenclature" (IU BMB Academic Press 1992).

It is naturally present in numerous plants such as, for example, soya, wheat or beet and in certain animal organs such as, for example, pig, calf or fish livers. These plant or animal materials may thus constitute industrial sources of this enzyme which, in addition, may also be synthesized by certain microorganisms.

Lipoxygenase is known in particular for its participation in the first step of a process making it possible to synthesize aldehydes from fatty acids. In fact, its oxidative catalytic activity on unsaturated fatty acids, and more particularly on linoleic and linolenic acids, gives rise to the formation of a hydroperoxide which may subsequently be cleaved to an oxo acid and an aldehyde by a hydroperoxide lyase.

DESCRIPTION OF A PREFERRED EMBODIMENT

Now, within the context of the invention, it has been found that lipoxygenase, whatever its origin, could by itself make possible the preparation of aromatic substances of formula:

from substrates represented by the abovementioned formulae and according to the following reaction:

($R_1$, $R_2$ and $R_3$ having the meanings given above).

The preferred aromatic substances prepared according to the method in accordance with the invention are summarized in Table I.

TABLE I

| Substituents of the substrate subjected to the action of the lipoxygenase | | | Name of the corresponding substrate | Name of a possible isomer of the substrate according to the invention | Product obtained by subjecting the substrate or its isomer to the action of the lipoxygenase |
|---|---|---|---|---|---|
| $R_1$ | $R_2$ | $R_3$ | | | |
| —$CH_3$ | —O—$CH_3$ | —OH | isoeugenol | eugenol | vanillin |
| —$CH_2OH$ | —O—$CH_3$ | —OH | coniferyl alcohol | | vanillin |
| —CHO | —O—$CH_3$ | —OH | coniferyl aldehyde | | vanillin |
| —COOH | —O—$CH_3$ | —OH | ferulic acid | | benzaldehyde |
| —$CH_2OH$ | —H | —H | cinnamyl alcohol | | benzaldehyde |
| —CHO | —H | —H | cinnamaldehyde | | benzaldehyde |
| —COOH | —H | —H | cinnamic acid | | benzaldehyde |
| —$CH_3$ | —H | —O—$CH_3$ | anethole | estragol | anisaldehyde |
| —$CH_3$ | —H | —OH | anol | chavicol | para hydroxybenzaldehyde |
| —$CH_3$ | —O⌒O— | | isosafrole | safrole | heliotropine |
| —COOH | —OH | —OH | caffeic acid | | protocatechnic aldehyde |

TABLE I-continued

| Substituents of the substrate subjected to the action of the lipoxygenase | | | Name of the corresponding substrate | Name of a possible isomer of the substrate according to the invention | Product obtained by subjecting the substrate or its isomer to the action of the lipoxygenase |
|---|---|---|---|---|---|
| R₁ | R₂ | R₃ | | | |
|  | —O—CH₃ | —OH | curcumin | | vanillin |

Eugenol, chavicol, estragol and safrole, which are the isomers of isoeugenol, anol, anethole and isosafrole respectively, may themselves be converted by lipoxygenase to the corresponding aldehyde, namely vanillin, hydroxybenzaldehyde, anisaldehyde and heliotropin, but with a lower yield.

In fact, the most important condition for lipoxygenase to be able to exert its action is that the substrate contains a correctly positioned unsaturated bond: this is especially the case for all the molecules represented by the formulae corresponding to the "substrate" for which the unsaturated bond situated on the chain bearing $R_1$ or $CH_2$ is either in the alpha or in the beta position of the aromatic ring. This is also the case for the known examples represented by linoleic and linolenic acids, in which either their carbon 9 or their carbon 13 (constituting a non-conjugated cis-cis diene system) is the site of a peroxidation.

The method in accordance with the invention thus consists in placing together, in a stirred and thermo-regulated buffered medium, a lipoxygenase and a substrate corresponding to one of the formulae represented above for a sufficient time to allow the preparation of the corresponding aromatic substance, it being possible for the latter to be subsequently recovered by standard solvent extraction or distillation techniques.

In the method in accordance with the invention, lipoxygenase may be used in purified or unpurified form.

Advantageously:

when it is purified, that is to say when it generally has an activity greater than 30,000 u/mg [sic], (1 unit corresponding to an increase in the absorbance at 234 nmof a value of 0.001 per minute when linoleic acid is the substrate, at pH 9 and at 25° C.), lipoxygenase is used in an amount of from 1 to 500 mg per gram of substrate, preferably from 5 to 100 mg per gram of substrate and even more preferably from 10 to 50 mg per gram of substrate, (by way of example, a lipoxygenase marketed by SIGMA in the form of an enzymatic preparation containing at least 60% of proteins may be used), and when it is not purified, that is to say when it contains less than 7,500 U/mg, as is the case in commercial acetone powders (preconcentrated form from a raw material), or in ground fresh plant material or in a plant material flour, or, alternatively, in a ground fresh animal organ such as the liver, it will be used in an amount of 0.01 to 50 g per gram of substrate, preferably from 0.025 to 10 g per gram of substrate and even more preferably from 0.1 to 5 g per gram of substrate.

According to the method in accordance with the invention, the lipoxygenases preferably used are soybean lipoxygenase and wheatgerm lipoxygenase.

According to an advantageous embodiment of the method in accordance with the invention, the concentration of the substrate for the lipoxygenase is established between 2.5 and 100 g per liter of reaction medium, and preferably between 20 and 75 g per liter of reaction medium.

In accordance with the invention, this reaction medium is a buffered aqueous medium. The buffers used are standard buffers such as potassium phosphate buffer and/or sodium phosphate buffer and/or sodium borate buffer and/or sodium borate/citrate/phosphate buffer.

The molarities of these buffers are advantageously between 0.05M and 0.5M and their pH is between 2 and 10 and preferably between 5 and 10. Adjustments to pH are made either with aqueous potassium or sodium hydroxide solutions or with phosphoric acid.

According to other advantageous characteristics of the invention:

- the temperature of the reaction medium varies between 4° and 40° C., and preferably between 22° and 32° C.;
- the duration of the reaction varies between 30 minutes and 7 days, preferably between 2 hours and 5 days, and is determined by monitoring the reaction kinetics;
- the stirring must be sufficiently vigorous to homogenize or emulsify the whole of the reaction medium and to oxygenate all of the substrate present, and is carried out at a speed between 150 and 250 rev/min.

In addition, an emulsifying agent such as TWEEN 80 may be introduced into the medium in a proportion of 0.05 to 2% by volume relative to the reaction medium.

According to an advantageous embodiment of the method in accordance with the invention, depending on the substrate used, and in particular when the substrate is a compound of phenolic nature, due to the toxicity of phenols towards the enzyme, it may be necessary to add to the reaction medium at least one adsorbing agent or one complexing agent chosen from the group comprising activated charcoal at a concentration between 5 and 50 g per liter, the latter known under the trade name "Amberlite" of type $XAD_2$ at a concentration between 5 and 50 g per liter, beta-cyclodextrin at a concentration between 3 and 18 g per liter and polyvinylpolypyrrolidone (PVPP) at a concentration between 10 and 60 g per liter, so as to protect the said enzyme.

The invention is not strictly limited to the described method; on the contrary, it embraces all the variants thereof. The Applicant has, for example, conclusively investigated the conversion of beta-carotene to beta-ionone by the action of lipoxygenase, which in this case acts on an unsaturated bond located in a gamma position relative to the ring of the molecule, conjugated with an unsaturated bond located in an alpha position relative to the same ring.

The examples which follow will make possible a better understanding of the invention; they are not limiting, and relate to the advantageous embodiments of the invention.

EXAMPLE 1

To a flask containing 20 ml of sodium borate buffer having a molarity of 0.1M and a pH of 6.5 are added 0.75 g of isoeugenol, 20 mg of lipoxygenase originating from soybean and assaying at 36,000 U/mg and 0.05 g of TWEEN 80.

After incubation for three days at 28° C. and with stirring at a speed of 150 rev/min, the whole test sample is extracted with dichloroethane and the vanillin is subsequently assayed by HPLC.

The vanillin production is 2.85 g/l.

EXAMPLE 2

Under the same conditions as in Example 1, 0.75 g of eugenol is added to the reaction medium in the place of isoeugenol in the presence of 0.5 g of activated charcoal.

The vanillin yield is 28.5 mg/liter.

EXAMPLE 3

Eight flasks containing the same ingredients as in Example 1 are incubated at 28° C. on a stirrer table revolving at 150 rev/min. Each day a sample is extracted with dichloroethane and assayed by HPLC.

Figure 1:
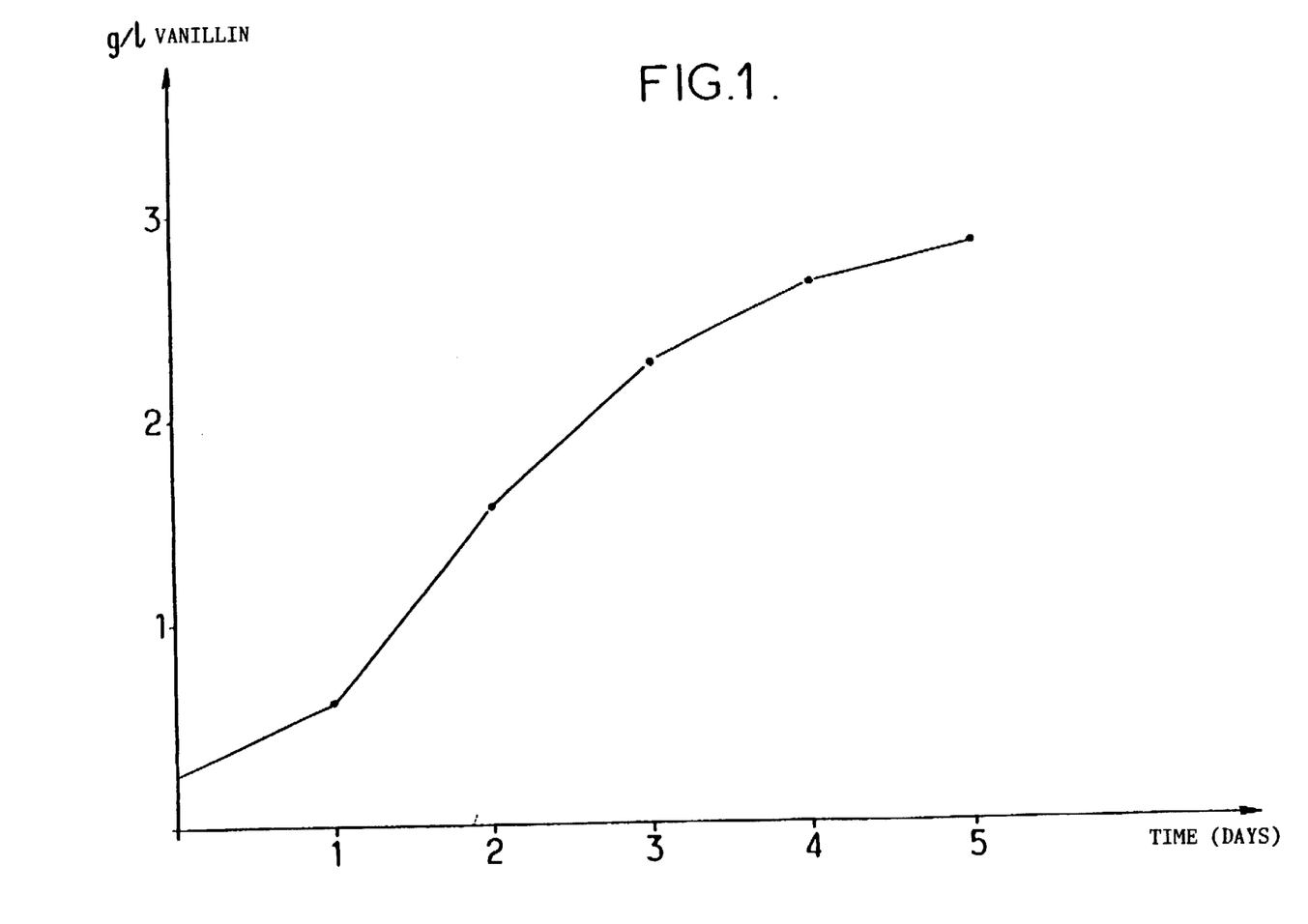
FIG. 1 illustrates the kinetics of production of vanillin from isoeugenol by lipoxygenase.

The kinetics are reproduced in FIG. 1.

The vanillin production reaches 2.82 g/l.

EXAMPLE 4

Under the same conditions as in the above examples, the concentrations of isoeugenol are varied from 5 to 100 g/l of reaction medium.

Figure 2:
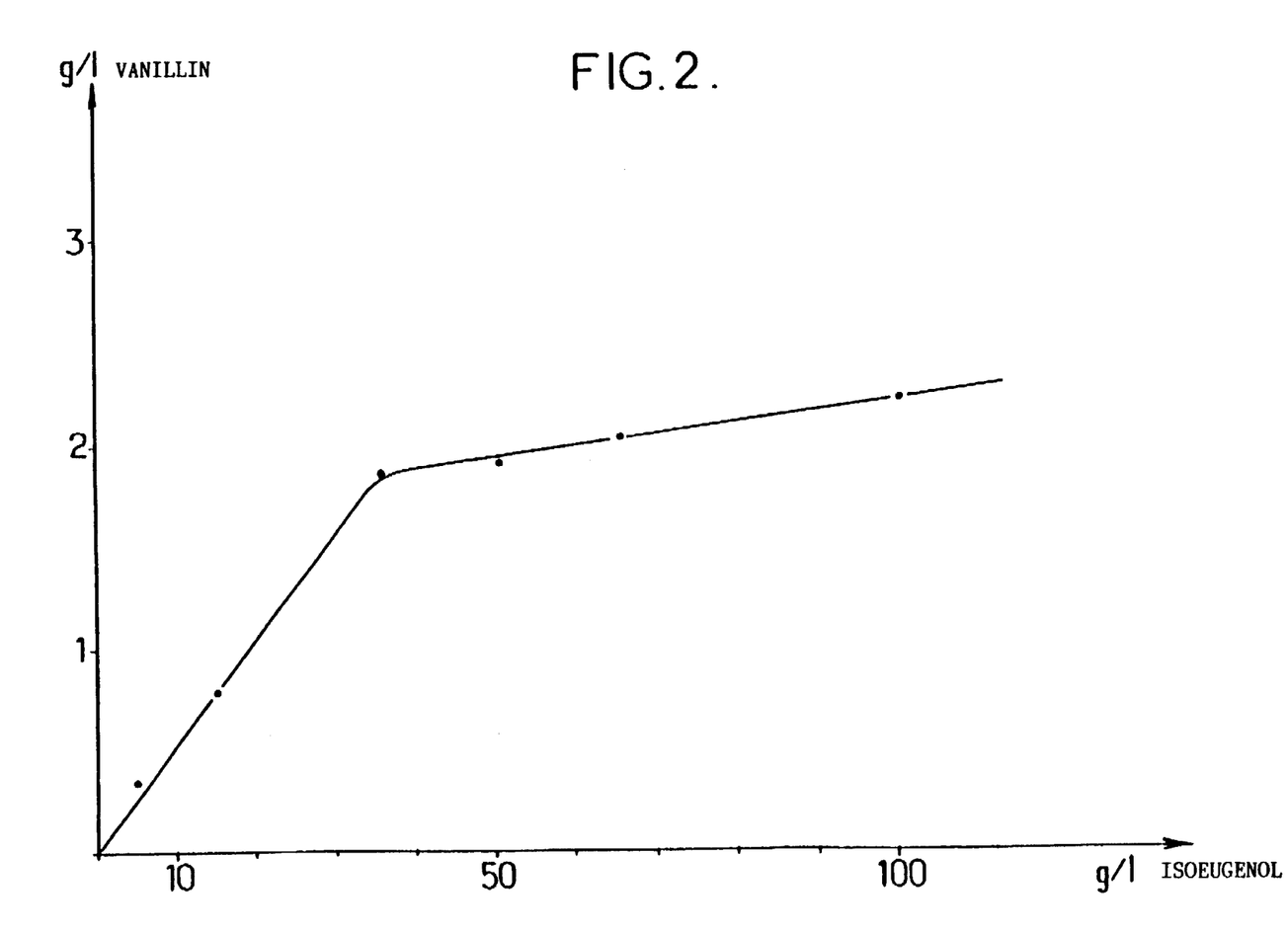
FIG. 2 illustrates the production of vanillin by lipoxygenase as a function of the concentration of isoeugenol.

A vanillin production, represented in FIG. 2, which reaches 2.2 g/l is obtained.

EXAMPLE 5

Under the conditions described in Example 1, the concentration of lipoxygenase added to the reaction medium is varied from 0 to 2.5 g/l of reaction medium.

Figure 3:
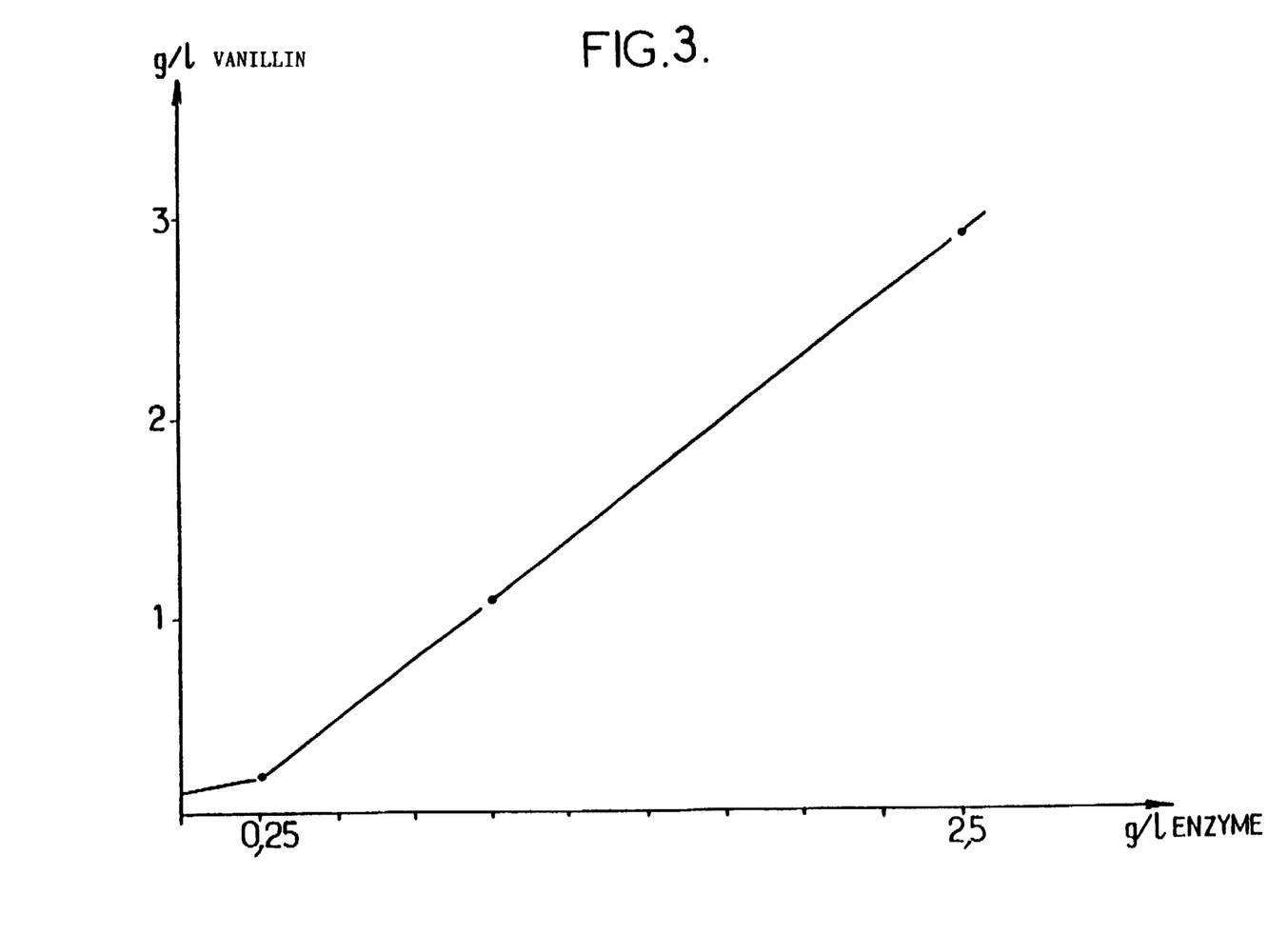
FIG. 3 illustrates the production of vanillin from isoeugenol as a function of the concentration of lipoxygenase.

The corresponding amounts of vanillin produced are represented in FIG. 3.

The vanillin production reaches 2.9 g/l.

EXAMPLE 6

Under the same conditions as in Example 1, 10 g/l of curcumin are added, treated beforehand with potassium hydroxide in order to solubilize it in the buffer medium.

Vanillin is obtained in a yield of 37 mg/l.

EXAMPLE 7

Under the same conditions as in Example 1, isoeugenol is replaced by 2 g/l of coniferyl alcohol.

In two days, vanillin is obtained in a yield of 240 mg/l.

EXAMPLE 8

Under the same conditions as in Example 1, 25 g/l of cinnamaldehyde are added.

After incubation for four days, 1.1 g/l of benzaldehyde are detected in the medium.

EXAMPLE 9

Under the same conditions as in Example 1, 8 g/l of anethole are added.

After four days, 448 mg/l of anisaldehyde are measured.

EXAMPLE 10

To a flask containing 25 g of ground eggplant and 25 g of sodium borate buffer having a molarity of 0.1M and a pH of 6.5 are added 0.4 g of isoeugenol and 0.05 g of TWEEN 80. After incubation for 3 days at 28° C. and with stirring at a speed of 200 rev/min, 1.75 g/l of vanillin are detected.

EXAMPLE 11

To a flask containing 20 g of sodium borate buffer having a molarity of 0.1M and a pH of 6.5 and 0.75 g of isoeugenol are added 5 g of ground fresh pig liver and 0.05 g of TWEEN 80. After incubation for 2 days at 28° C. and with stirring at a speed of 200 rev/min, the amount of vanillin measured is 0.7 g/l.

We claim:

1. Method for the preparation of aromatic substances having formula I:

wherein a substrate selected from the group consisting of eugenol, estragol, chavicol, safrole, compounds having the formula II:

and compounds having the formula III:

in which $R_2$ is a radical selected from the group consisting of $-CH_3$, $-CH_2OH$, $-CHO$, $-COOH$, or $R_2$ is a radical selected from the group consisting of —H, —OH, or —O—$CH_3$, $R_3$ is a radical selected from the group consisting of —H, —OH, or —O—$CH_3$, with the proviso that when $R_2$ and $R_3$ represent together —OH, then $R_1$ does not represent —COOH, or $R_2$ and $R_3$ form a methylenedioxy bridge, is reacted with a lipoxygenase, and the aromatic substances having formula I are recovered, and wherein said lipoxygenase is used in purified form in an amount of 1 to 500 mg per gram of substrate or in unpurified form in an amount of 0.01 to 50 g per gram of substrate.

2. Method according to claim 1, wherein aromatic substances having formula I are selected from the group consisting of vanillin, benzaldehyde, anisaldehyde, parahydroxybenzaldehyde, heliotropin and protocatechic aldehyde.

3. Method according to claim 1, wherein the lipoxygenase in purified form is used in an amount of 5 to 100 mg per gram of substrate.

4. Method according to claim 1, wherein the lipoxygenase in purified form is used in an amount of 10 to 50 mg per gram of substrate.

5. Method according to claim 1, wherein the lipoxygenase in unpurified form is used in ah amount of 0.025 to 10 g per gram of substrate.

6. Method according to claim 1, wherein the lipoxygenase in unpurified form is used in an amount of 0.1 to 5 g per gram of substrate.

7. Method according to claim 1, wherein a lipoxygenase or a source of lipoxygenase of plant origin is used.

8. Method according to claim 1, wherein a lipoxygenase or a source of lipoxygenase of animal origin is used.

9. Method according to claim 1, wherein the concentration of the substrate is between 2.5 and 100 g per liter of reaction medium.

10. Method according to claim 1, wherein the concentration of the substrate for the lipoxygenase is established between 20 and 75 g per liter of reaction medium.

11. Method according to claim 1, wherein the reaction medium is a buffered medium having a pH between 2 and 10.

12. Method according to claim 1, wherein the reaction medium is a buffered medium having a pH between 5 and 10.

13. Method according to claim 1, wherein the temperature of the reaction medium is between 4° and 40° C.

14. Method according to claim 1, wherein the temperature of the reaction medium is between 22° and 32° C.

15. Method according to claim 1, wherein the duration of the reaction varies from 30 minutes to 7 days.

16. Method according to claim 1, wherein the duration of the reaction varies from 2 hours to 5 days.

17. Method according to claim 1, wherein the reaction medium is stirred at a speed between 150 and 250 rev/min.

18. Method according to claim 1, wherein an emulsifying agent is added in an amount of 0.05 to 2%, by volume relative to the reaction medium.

19. Method according to claim 1, wherein at least one adsorbing agent or one complexing agent is added to the reaction medium when a compound wherein $R_2$ or $R_3$ or both are OH is used as substrate.

20. Method according to claim 19, wherein the adsorbing agent or the complexing agent is selected from the group consisting of activated charcoal at a concentration between 5 and 50 g per liter, Amberlite® of type $XAD_2$ at a concentration between 5 and 50 g per liter, B-cyclodextrin at a concentration between 3 and 18 g per liter, and polyvinylpolypyrrolidone at a concentration between 10 and 60 g per liter.

\* \* \* \* \*

UNITED STATES PATENT AND TRADEMARK OFFICE
CERTIFICATE OF CORRECTION

PATENT NO. : 5,712,132                     Page 1 of 2
DATED      : January 27, 1998
INVENTOR(S): Mane et al

It is certified that error appears in the above-indentified patent and that said Letters Patent is hereby corrected as shown below:

Column 1,    line 34, change "protocatechnic" to --protocatechuic--.

Columns 3 and 4,  Table I, last column, line 4, under "lipoxygenase" change "benzaldehyde" to --vanillin--.

Columns 3 and 4,  Table I, last column, line 12, under "lipoxygenase" change "protocatechnic" to --protocatechuic--.

Column 8,    line 50, change "  " to --  --.

Column 8,    line 57, change "  " to --  --.

Column 8,    line 8, line 66, change "$R_2$" to --$R_1$--.

UNITED STATES PATENT AND TRADEMARK OFFICE
CERTIFICATE OF CORRECTION

PATENT NO.  : 5,712,132
DATED       : January 27, 1998
INVENTOR(S) : Mane et al

It is certified that error appears in the above-indentified patent and that said Letters Patent is hereby corrected as shown below:

Column 9,   line 12, before "with the proviso" insert --$R_2$ and $R_3$ may form a methylenedioxy bridge--.

Column 9,   line 14, delete "or $R_2$ and $R_3$ form a methylenedioxy bridge".

Column 9,   line 22, change "protocatechnic" to --protocatechuic--.

Signed and Sealed this

Ninth Day of March, 1999

Attest:

Q. TODD DICKINSON

*Attesting Officer*    *Acting Commissioner of Patents and Trademarks*